(12) United States Patent
Suzuki et al.

(10) Patent No.: US 8,153,601 B2
(45) Date of Patent: Apr. 10, 2012

(54) AZITHROMYCIN-CONTAINING AQUEOUS PHARMACEUTICAL COMPOSITION AND A METHOD FOR THE PREPARATION OF THE SAME

(75) Inventors: Hidekazu Suzuki, Tokyo (JP); Kuniko Koichi, Tokyo (JP); Kouhei Yoda, Tokyo (JP)

(73) Assignee: Wakamoto Pharmaceutical Co., Ltd., Tokyo (JP)

( * ) Notice: Subject to any disclaimer, the term of this patent is extended or adjusted under 35 U.S.C. 154(b) by 803 days.

(21) Appl. No.: 11/613,370

(22) Filed: Dec. 20, 2006

(65) Prior Publication Data

US 2007/0087980 A1 Apr. 19, 2007

Related U.S. Application Data

(63) Continuation of application No. PCT/JP2005/012327, filed on Jul. 4, 2005.

(30) Foreign Application Priority Data

Jul. 2, 2004 (JP) ................................. 2004-196315

(51) Int. Cl.
*A61K 31/7048* (2006.01)
*A61K 31/194* (2006.01)
*A61K 31/133* (2006.01)

(52) U.S. Cl. ........................... 514/30; 514/574; 514/667
(58) Field of Classification Search ............... 514/30, 514/574, 667
See application file for complete search history.

(56) References Cited

U.S. PATENT DOCUMENTS

| | | | |
|---|---|---|---|
| 4,474,768 A | 10/1984 | Bright | |
| 4,517,359 A | 5/1985 | Kobrehel et al. | |
| 5,916,550 A | 6/1999 | Inada et al. | |
| 6,277,829 B1 * | 8/2001 | Asero et al. | 514/29 |
| 6,569,443 B1 * | 5/2003 | Dawson et al. | 424/433 |
| 2003/0206956 A1 | 11/2003 | Dawson et al. | |
| 2004/0214782 A1 * | 10/2004 | Canning et al. | 514/28 |
| 2005/0152982 A1 * | 7/2005 | Appel et al. | 424/489 |

FOREIGN PATENT DOCUMENTS

| | | |
|---|---|---|
| EP | 1 537 859 A2 | 6/2005 |
| JP | 10-316572 | 12/1998 |
| JP | 11-240838 | 9/1999 |
| JP | 2001-89378 | 4/2001 |
| JP | 2001-261552 | 9/2001 |
| JP | 2002-540147 | 11/2002 |
| WO | WO 02/087596 A2 | 11/2002 |

OTHER PUBLICATIONS

Gennaro, AR. Remington: The Science and Practice of Pharmacy, 2000, Lippincott Williams & Wilkins, 20th ed, p. 1038-1040.*

* cited by examiner

*Primary Examiner* — Shaojia Anna Jiang
*Assistant Examiner* — Jonathan S Lau
(74) *Attorney, Agent, or Firm* — Oblon, Spivak, McClelland, Maier & Neustadt, L.L.P.

(57) ABSTRACT

The invention provides an azithromycin-containing aqueous pharmaceutical composition, which comprises at least one member selected from the group consisting of azithromycin, and pharmaceutically acceptable salts thereof, and at least one member selected from the group consisting of monoethanolamine, diethanolamine, triethanolamine, and pharmaceutically acceptable salts thereof, and which does not comprise boric acid or pharmaceutically acceptable salts thereof, and a method for the preparation of the composition, wherein an azithromycin-containing liquid is maintained at pH of 4.0 or higher throughout the method for the preparation. The composition has good heat and storage stability.

8 Claims, No Drawings

AZITHROMYCIN-CONTAINING AQUEOUS PHARMACEUTICAL COMPOSITION AND A METHOD FOR THE PREPARATION OF THE SAME

This application is a continuation of PCT/JP05/12327, Jul. 4, 2005. This application also claims priority to Japan 2004-196315 filed Jul. 2, 2004.

TECHNICAL FIELD

This invention relates to an azithromycin-containing aqueous pharmaceutical composition and a method for the preparation of the same.

Azithromycin is antibiotic having wide-range antibiotic spectrum derived from erythromycin A. Azithromycin is disclosed in U.S. Pat. No. 4,474,768 (Bright) and U.S. Pat. No. 4,517,359 (Kobrehel et al). The patents disclose that azithromycin and its specific derivatives have antibiotic activity and are useful as antibiotics. Azithromycin is excellent antibiotic drug and is now commercially available as oral composition for systemic administration.

In addition, dosage forms other than oral dosage have been studied to apply the excellent antibiotic activity of azithromycin to other uses. In particular, application to ophthalmic use is highly expected. Examples for application to ophthalmic use are disclosed in JP-A-11-240838, JP-A-2001-089378, JP-A-2002-540147, etc.

As mentioned above, although application of azithromycin to ophthalmic use is highly expected, it has not been put into practice. This is because azithromycin is low in water solubility and decomposed easily in water. It is therefore difficult to develop an eye drop containing azithromycin.

In order to prepare an ophthalmic formulation containing azithromycin, there have been tried to prepare an aqueous solution of azithromycin. JP-A-2001-089378 discloses a method for the preparation of azithromycin-containing ophthalmic aqueous formulation, which comprises the steps of solubilizing ophthalmologically acceptable polybasic phosphate in a concentration of 7.8-68.6 g/L and citric acid monohydrate in a concentration of 0.9-35.94 g/L, and then adding azithromycin in an amount of 0.1-100 g/L at 15-25° C., wherein a molar ratio of azithromycin to citric acid is about 1:0.67-1:1.5 and the formulation has pH of 5.5-7.6 and a final osmolarity of about 130-300 mOsm/kg. It is disclosed that according to the method, it is possible to prepare an azithromycin-containing aqueous pharmaceutical composition at pH range (pH6.4-7.6) which is physiological and relatively high in heat stability. Further, it is disclosed that the composition is stable for 4 weeks after the preparation at 25° C.±2° C. and relative humidity of 75%±5%.

According to the disclosure of JP-A-2001-089378, it has now been possible to prepare an aqueous pharmaceutical composition containing hardly water soluble azithromycin. However, there is a need for pharmaceutical composition having much higher heat stability.

Patent Document 1: JP-A-11-240838
Patent Document 2: JP-A-2001-089378

DISCLOSURE OF THE INVENTION

Problems to be Solved By the Invention

An object of the present invention is to provide an azithromycin-containing aqueous pharmaceutical composition having high heat stability and a method for preparing the same.

Means for Solving the Problems

The present invention provides an azithromycin-containing aqueous pharmaceutical composition and a method for preparing the same as described below.

1. An azithromycin-containing aqueous pharmaceutical composition, which comprises at least one member selected from the group consisting of azithromycin, its anhydride, its hydrate, and pharmaceutically acceptable salts thereof, and at least one member selected from the group consisting of monoethanolamine, diethanolamine, triethanolamine, amino acid, ethylenediaminetetraacetic acid, and pharmaceutically acceptable salts thereof, and which does not comprise boric acid or pharmaceutically acceptable salts thereof.
2. The aqueous pharmaceutical composition of the above item 1, wherein said amino acid is at least one member selected from the group consisting of epsilon-amino caproic acid, glycine, glutamic acid, aspartic acid, alanine, serine, and pharmaceutically acceptable salts thereof.
3. The aqueous pharmaceutical composition of the above item 1 or 2, wherein the composition further comprises at least one member selected from the group consisting of sodium chloride and mannitol.
4. The aqueous pharmaceutical composition of any one of the above items 1 to 3, wherein the composition further comprises a polyvalent carboxylic acid.
5. The aqueous pharmaceutical composition of the above item 4, wherein the polyvalent carboxylic acid is at least one member selected from the group consisting of citric acid, tartaric acid, malic acid, maleic acid, fumaric acid, and succinic acid.
6. The aqueous pharmaceutical composition of any one of the above items 1 to 5, wherein the composition has pH of from 6.0 to 7.5.
7. The aqueous pharmaceutical composition of the above item 6, wherein the composition has pH of from 6.0 to 6.5.
8. A method for the preparation of an azithromycin-containing aqueous pharmaceutical composition of any one of the above items 1 to 7, wherein an azithromycin-containing liquid is maintained at pH of 4.0 or higher throughout the method for the preparation.
9. The method of the above item 8, wherein an azithromycin-containing liquid is maintained at pH of 5.0 or higher throughout the method for the preparation.
10. The method of the above item 8 or 9, wherein azithromycin is suspended in water and then a polyvalent carboxylic acid is added to the suspension.

Effects of the Invention

The azithromycin-containing aqueous pharmaceutical composition of the present invention comprises hardly water soluble azithromycin and is higher in heat stability than those of the prior art.

BEST MODE FOR CARRYING OUT THE INVENTION

The inventors of the present invention have studied solubilization of azithromycin in water and found that it is very important to add a specific additive such as monoethanolamine to an azithromycin-containing aqueous solution to increase heat stability of azithromycin in the solution.

Further, the inventors have found that azithromycin is solubilized by the addition of a polyvalent carboxylic acid but azithromycin is decomposed when pH of the azithromycin-containing aqueous solution is less than 4.0.

The present invention has been completed based on the above findings and provides an azithromycin-containing aqueous pharmaceutical composition which comprises a specific additive such as monoethanolamine.

The present invention further provides a method for preparing the composition wherein the azithromycin-containing liquid is maintained at pH of 4.0 or higher, preferably 5.0 or higher throughout the method for the preparation.

Preferred examples of azithromycin used in the present invention include azithromycin anhydride, azithromycin monohydrate, and azithromycin dihydrate. Also preferred are pharmaceutically acceptable salts of azithromycin, such as polyvalent carboxylic acid salts, for example, citric acid salt, tartaric acid salt, malic acid salt, maleic acid salt, and fumaric acid salt.

Concentration of azithromycin used in the composition of the present invention is not limited to specific range as long as the effect of the present invention is attained, but it is usually 0.01 to 10 w/v %, preferably 0.1 to 5 w/v %, more preferably 0.3 to 3.0 w/v % as the weight of azithromycin. If it is 10 w/v % or lower, it is preferable because it is easy to prepare an aqueous solution of azithromycin, while if it is 0.01 w/v % or higher, it is preferable because antibiotic activity of azithromycin is surely obtained.

Additives for increasing stability of azithromycin in an aqueous solution is at least one member selected from the group consisting of monoethanolamine, diethanolamine, triethanolamine, amino acid, ethylenediaminetetraacetic acid and pharmaceutically acceptable salts thereof.

Preferred examples of amino acid used in the present invention include epsilon-amino caproic acid, glycine, glutamic acid, aspartic acid, alanine, serine and pharmaceutically acceptable salts thereof.

Preferred examples of pharmaceutically acceptable salts of amino acid and ethylenediaminetetraacetic acid include sodium salts, potassium salts, hydrochloric acid salts and sulfuric acid salts.

Preferred examples of pharmaceutically acceptable salts of monoethanolamine, diethanolamine, and triethanolamine include hydrochloric acid salts and sulfuric acid salts.

Concentration of the additives used in the composition of the present invention is not limited to specific range as long as the effect of the present invention is attained, but it is usually 0.001 to 10 w/v %, preferably 0.005 to 4.0 w/v %. If it is 10 w/v % or lower, it is preferable because it is easy to handle the additives, while if it is 0.001 w/v % or higher, it is preferable because stability-increasing effect of the additives is surely obtained.

The azithromycin-containing aqueous pharmaceutical composition of the present invention may contain an additive for osmoregulation or isotonization. Examples of the additives include sugar such as xylitol, mannitol, and glucose, propyleneglycol, glycerine, sodium chloride, and potassium chloride. Among them, sodium chloride or mannitol is preferred because of small influence on the stability of azithromycin in the aqueous solution.

In addition, the azithromycin-containing aqueous pharmaceutical composition of the present invention may contain other drugs. For example, new quinolones such as levofloxacin, ofloxacin, lomefloxacin, norfloxacin, tosufloxacin, gatifloxacin, moxifloxacin; cephem antibiotic such as cefmenoxime hydrochloride; synthetic penicillin such as sulbenicillin sodium; aminoglycoside antibiotic such as micronomicin sulfate, sisomicin sulfate, dibekacin sulfate, gentamicin sulfate, tobramycin; antibiotic such as chloramphenicol; antivirotic such as aciclovir, idoxuridine; steroid such as fluorometholone, dexamethasone, prednisolone, prednisolone acetate, betamethasone sodium phosphate, hydrocortisone acetate, dexamethasone sodium metasulfobenzoate, dexamethasone sodium phosphate, fluorocynolon acetonide, difluprednate; non-steroidal antiinflammatory drug such as diclofenac sodium, pranoprofen, bromfenac sodium, indomethacin; mydriatic such as phenylephrine hydrochloride, tropicamide, atropine sulfate, dipivefrine hydrochloride, cyclopentolate hydrochloride, homatropine hydrobromide; miotic such as pilocarpine hydrochloride, distigmine bromide; local anesthetic such as oxybuprocaine hydrochloride, lidocaine hydrochloride; antiglaucomatous such as latanoprost, isopropyl unoprostone, timolol maleate, carteolol hydrochloride, dorzolamide hydrochloride, brinzolamide, nipradilol hydrochloride, levobunolol hydrochloride, betaxolol hydrochloride, bunazosin hydrochloride, dipivefrine hydrochloride, apraclonidine hydrochloride, befunolol hydrochloride. Content of these drugs in the composition of the present invention is not limited to specific one as long as expected effect thereof is obtained.

The azithromycin-containing aqueous pharmaceutical composition of the present invention may suitably be used, making use of the property, as injection, oral drug, ear drip, nasal drop, liniment, and the like, as well as eye drop.

The azithromycin-containing aqueous pharmaceutical composition of the present invention may further contain a polyvalent carboxylic acid to dissolve azithromycin. Examples suitably used as such a polyvalent carboxylic acid include citric acid, tartaric acid, malic acid, maleic acid, fumaric acid, and succinic acid.

Concentration of the polyvalent carboxylic acid used in the composition of the present invention is not limited to specific range as long as it dissolves azithromycin, but it is usually 0.01 to 3 w/v %, preferably 0.02 to 1.0 w/v %. If it is 3 w/v % or lower, it is preferable because it is easy to handle the additives, while if it is 0.01 w/v % or higher, it is preferable because azithromycin is completely dissolved.

In order to prepare the azithromycin-containing aqueous pharmaceutical composition of the present invention, it is preferable to maintain pH of the azithromycin-containing liquid at 4.0 or higher, preferably 5.0 or higher throughout the preparation steps. If pH is 4.0 or higher, it is preferable because azithromycin is not decomposed during the preparation steps. There is no specific upper limit of pH but it is preferable that pH is 11 or lower, preferably 10 or lower.

It is preferable that the aqueous pharmaceutical composition of the present invention contains a polyvalent carboxylic acid, in particular, citric acid to dissolve azithromycin. However, it has now been found that if the polyvalent carboxylic acid is dissolved prior to adding azithromycin, a rate of dissolution of azithromycin is greatly increased but pH of the solution at initial dissolution stage becomes lower than 4.0 and azithromycin is decomposed. In order to prevent decomposition of azithromycin, azithromycin is first suspended in water and then a polyvalent carboxylic acid is gradually added so that pH of the suspension is not lower than 4.0. It has now been found that according to the method, azithromycin is dissolved completely but is not decomposed.

Stability of azithromycin content in the pharmaceutical composition of the present invention depends on pH of the composition. The composition of the present invention is generally adjusted to pH5.5 to 8.0, preferably pH6.0 to 7.5, more preferably pH6.0 to 7.0, most preferably pH6.0 to 6.5. To adjust pH of the aqueous pharmaceutical composition of the present invention, conventional pH adjustors may be used. Examples of such adjustors include acids such as ascorbic acid, hydrochloric acid, gluconic acid, acetic acid, lactic acid, phosphoric acid; bases such as potassium hydroxide, calcium hydroxide, sodium hydroxide, magnesium hydroxide, monoethanolamine, diethanolamine, triethanolamine, and the like. Examples of other pH adjustors include amino acids such as glycine, histidine, epsilon-amino caproic acid. It is however contraindicated to add boric acid or its salts which accelerate decomposition of azithromycin.

When the azithromycin-containing aqueous pharmaceutical composition of the present invention is prepared, pharmaceutically acceptable solubilizing agents, preservatives, antiseptics and the like may be added to the composition of the present invention, if necessary, as long as the effect of the invention is not impaired. Such solubilizing agents include polysorbate 80, and polyoxyethylenene hydrogenated castor oil. Such preservatives include inversed soap such as benzalkonium chloride, benzethonium chloride, and chlorhexidine gluconate; parabens such as methyl parahydroxybenzoate, propyl parahydroxybenzoate, and butyl parahydroxybenzoate; alcohols such as chlorobutanol, phenylethyl alcohol, and benzyl alcohol; organic acids and salts thereof such as sodium dehydroacetate, sorbic acid and potassium sorbate; mercury compounds, such as thimerosal. Other additives include thickening agents such as methyl cellulose, hydroxymethyl cellulose, hydroxyethyl cellulose, polyvinyl pyrrolidone, polyvinyl alcohol, polyethylene glycol and sodium polyacrylate.

A method for the preparation of an azithromycin-containing aqueous pharmaceutical composition of the present invention will be illustrated. Azithromycin is suspended in sterile purified water. A polyvalent carboxylic acid dissolved in water is gradually added to the suspension with caution to keep pH of the azithromycin-containing liquid 4.0 or higher. After azithromycin is completely dissolved, there are added, dissolved and mixed other drugs, monoethanolamine, mannitol, preservative, and the like until a uniform solution is obtained. PH adjustor is added to adjust the pH and sterile purified water is added to a given volume to obtain an azithromycin-containing aqueous pharmaceutical composition of the present invention.

The aqueous pharmaceutical composition of the present invention thus prepared is sterilized through membrane filter and packed in a plastic container for eye drops to form eye drops.

The azithromycin-containing aqueous pharmaceutical composition prepared by the method of the present invention is characterized in that a ratio of azithromycin content in the composition just after the preparation to azithromycin content used for the preparation (survival rate) is high and the survival rate is preferably at least 90%, more preferably at least 95%, and most preferably at least 97%.

The azithromycin-containing aqueous pharmaceutical composition of the present invention is also characterized by high heat stability. A rate of survival after 5 mL of the composition is packed in 10 mL glass vial, sealed and stored at 60° C. for one week (a rate of azithromycin content in the composition just after the storage to azithromycin content just before the storage) is preferably at least 65%, more preferably at least 70%, still more preferably at least 75%, and most preferably at least 80%.

EXAMPLES 1 TO 8 AND COMPARATIVE EXAMPLES 1 AND 2

Azithromycin (1.0 g) was added to sterile purified water (50 mL), agitated and dispersed. Separately, citric acid monohydrate (1.9 g) was dissolved in sterile purified water (80 mL) and sterile purified water was added to obtain a citric acid solution (100 mL). To the azithromycin dispersed liquid, the citric acid solution (10 mL) was gradually added with agitation so that pH of the liquid was maintained at 5.0 or higher. After confirming that azithromycin was completely dissolved, NaCl (0.73 g) and the following additives were added in given amounts and dissolved with agitation.

Additives:
monoethanolamine
diethanolamine
triethanolamine
epsilon-amino caproic acid
glycine
L-glutamic acid
L-aspartic acid
ethylenediaminetetraacetic acid disodium salt (0.5 w/v % aqueous solution previously prepared)

After confirming that the solution became clear, pH was adjusted to 7.0 with 1N-NaOH or 1N-HCl and sterile purified water was added to prepare 100 mL of the azithromycin-containing aqueous pharmaceutical composition of the present invention (Examples 1 to 8).

Azithromycin (1.0 g) was added to sterile purified water (50 mL), agitated and dispersed. Separately, citric acid monohydrate (1.9 g) was dissolved in sterile purified water (80 mL) and sterile purified water was added to obtain a citric acid solution (110 mL). To the azithromycin dispersed liquid, the citric acid solution (10 mL) was gradually added with agitation so that pH of the liquid was maintained at 5.0 or higher. After confirming that azithromycin was completely dissolved, NaCl (0.73 g) was added in a given amount and dissolved with agitation.

After confirming that the solution became clear, pH was adjusted to 7.0 with 1N-NaOH or 1N-HCl and sterile purified water was added to prepare 100 mL of the azithromycin-containing aqueous pharmaceutical composition (Comparative Example 1).

To water (80 mL) agitated at 15° C. to 25° C., disodium hydrogenphosphate 12 hydrate (3.3 g) and citric acid monohydrate (0.44 g) were added. After these buffers were completely dissolved, azithromycin (1.0 g) was added and dissolved with agitation. After confirming that the solution became clear, sterile purified water was added to prepare 100 mL of the azithromycin-containing aqueous pharmaceutical composition (Comparative Example 2).

The method for the preparation was according to the disclosure of JP-A-2001-089378.

TEST EXAMPLE 1

Stability of the azithromycin-containing aqueous pharmaceutical compositions prepared in the above Examples and Comparative Examples were evaluated in terms of azithromycin concentration in the composition.

The compositions (Examples 1 to 8 and Comparative Examples 1 and 2) were packed in glass vial, sealed with a lid, and stored at 60° C. for one and two weeks. Then, azithromycin concentration in the composition just after packed in the glass vial and after the storage at 60° C. was determined by HPLC. Stability was evaluated as follows.

First, the azithromycin content added was compared with the azithromycin content in the composition just after packed in the glass vial to evaluate stability of azithromycin during the preparation steps. This is expressed by a survival rate of AZT after preparation wherein AZT means azithromycin.

Second, the azithromycin content in the composition just after packed in the glass vial was compared with the azithromycin content in the composition after the storage at 60° C. to evaluate heat stability of azithromycin. This is expressed by a survival rate of AZT. Results are shown in Table 1.

TABLE 1

| | Ex. 1 | Ex. 2 | Ex. 3 | Ex. 4 | Ex. 5 | Ex. 6 | Ex. 7 | Ex. 8 | Comp. Ex. 1 | Comp. Ex. 2 |
|---|---|---|---|---|---|---|---|---|---|---|
| AZT (w/v %) | 1.0 | 1.0 | 1.0 | 1.0 | 1.0 | 1.0 | 1.0 | 1.0 | 1.0 | 1.0 |
| monoethanol amine (w/v %) | 0.2 | — | — | — | — | — | — | 0.2 | — | — |
| diethanol amine (w/v %) | — | 0.2 | — | — | — | — | — | — | — | — |
| triethanol amine (w/v %) | — | — | 0.2 | — | — | — | — | — | — | — |
| ε-aminocaproic acid (w/v %) | — | — | — | 0.5 | — | — | — | — | — | — |
| glycine (w/v %) | — | — | — | — | 0.5 | — | — | — | — | — |
| L-glutamic acid (w/v %) | — | — | — | — | — | 0.1 | — | — | — | — |
| L-aspartic acid (w/v %) | — | — | — | — | — | — | 0.1 | — | — | — |
| EDTA·2Na (w/v %) | — | — | — | — | — | — | — | 0.005 | — | — |
| citric acid·$H_2O$ (w/v %) | 0.19 | 0.19 | 0.19 | 0.19 | 0.19 | 0.19 | 0.19 | 0.19 | 0.19 | 0.44 |
| $Na_2HPO_4 \cdot 12H_2O$ (w/v %) | — | — | — | — | — | — | — | — | — | 3.3 |
| NaCl (w/v %) | 0.73 | 0.73 | 0.73 | 0.73 | 0.73 | 0.73 | 0.73 | 0.73 | 0.73 | — |
| 1N NaOH or 1N HCl | A.A. | A.A. | A.A. | A.A. | A.A. | A.A. | A.A. | A.A. | A.A. | — |
| water | A.A. | A.A. | A.A. | A.A. | A.A. | A.A. | A.A. | A.A. | A.A. | A.A. |
| pH | 7.0 | 7.0 | 7.0 | 7.0 | 7.0 | 7.0 | 7.0 | 7.0 | 7.0 | 7.0 |
| survival rate of AZT after preparation (%) | 100.1 | 99.8 | 99.7 | 100.5 | 99.6 | 100.2 | 100.1 | 100.9 | 89.8 | 100.3 |
| survival rate of AZT stored at 60° C. for one week (%) | 76.2 | 75.4 | 74.9 | 75.9 | 73.9 | 74.8 | 74.5 | 79.6 | 67.3 | 56.4 |
| survival rate of AZT stored at 60° C. for two weeks (%) | 62.3 | 61.8 | 60.9 | 62.0 | 60.8 | 60.4 | 60.3 | 63.4 | 54.6 | 32.9 |

Note:
A.A. = appropriate amount

Stability During Preparation Steps:

The survival rates of AZT after preparation demonstrate that azithromycin in the compositions of the present invention (Examples 1 to 8) and Comparative Example 2 was not decomposed during the preparation steps and completely dissolved, while azithromycin in Comparative Example 1 to which any stabilizer has not been added was a little decomposed during the preparation steps.

Heat Stability of Azithromycin:

The data demonstrate that the compositions of the present invention have higher heat stability than those of Comparative Examples 1 and 2. In particular, the survival rates of AZT of the present invention stored at 60° C. for two weeks are two times higher than that of Comparative Example 2.

Comparison of the survival rates of AZT stored at 60° C. for one week in Example 1 with Example 8 demonstrates that the addition of EDTA increases a little heat stability of azithromycin.

EXAMPLES 9 TO 12 AND COMPARATIVE EXAMPLE 3

To sterile purified water (50 mL), azithromycin (1.0 g) was added, mixed and dispersed. Separately, citric acid monohydrate (1.9 g) was dissolved in sterile purified water (80 mL) and sterile purified water was added to obtain a citric acid solution (100 mL). To the azithromycin dispersed liquid, the citric acid solution (10 mL) was gradually added with agitation so that pH of the liquid was maintained at 5.0 or higher. After confirming that azithromycin was completely dissolved, ethanolamine (0.2 g) and the following additives were added in given amounts and dissolved with agitation.

Additives:
 NaCl
 propylene glycol
 glycerine
 mannitol

After confirming that the solution became clear, pH was adjusted to 7.0 with 1N-NaOH or 1N-HCl and sterile purified water was added to prepare 100 mL of the azithromycin-containing aqueous pharmaceutical compositions (Examples 9 to 12).

Separately, according to the similar procedure to Comparative Example 2, the azithromycin-containing aqueous pharmaceutical composition (Comparative Example 3) was prepared.

TEST EXAMPLE 2

The same procedures in Test Example 1 were repeated to evaluate stability of the compositions of Examples 9 to 12 and Comparative Example 3. Results are shown in Table 2.

TABLE 2

| | Ex. 9 | Ex. 10 | Ex. 11 | Ex. 12 | Comp. Ex. 3 |
|---|---|---|---|---|---|
| AZT (w/v %) | 1.0 | 1.0 | 1.0 | 1.0 | 1.0 |
| monoethanolamine (w/v %) | 0.2 | 0.2 | 0.2 | 0.2 | — |

TABLE 2-continued

|  | Ex. 9 | Ex. 10 | Ex. 11 | Ex. 12 | Comp. Ex. 3 |
|---|---|---|---|---|---|
| NaCl (w/v %) | 0.73 | — | — | — | — |
| propylene glycol (w/v %) | — | 1.61 | — | — | — |
| glycerine (w/v %) | — | — | 2.07 | — | — |
| D-mannitol (w/v %) | — | — | — | 1.61 | — |
| citric acid•H$_2$O (w/v %) | 0.19 | 0.19 | 0.19 | 0.19 | 0.44 |
| Na$_2$HPO$_4$•12H$_2$O (w/v %) | — | — | — | — | 3.3 |
| 1N NaOH or 1N HCl | A.A. | A.A. | A.A. | A.A. | — |
| water | A.A. | A.A. | A.A. | A.A. | A.A. |
| survival rate of AZT after preparation (%) | 99.8 | 99.2 | 99.0 | 100.5 | 100.5 |
| survival rate of AZT stored at 60° C. for one week (%) | 72.5 | 69.8 | 70.7 | 73.7 | 53.6 |
| survival rate of AZT stored at 60° C. for two weeks (%) | 60.3 | 53.6 | 55.4 | 60.5 | 29.6 |

Stability During Preparation Steps:

The survival rates of AZT after preparation demonstrate that azithromycin in the compositions of the present invention (Examples 9 to 12) and Comparative Example 3 was not decomposed during the preparation steps and completely dissolved.

Heat Stability of Azithromycin:

The data demonstrate that the compositions of the present invention have higher heat stability than that of Comparative Example 3. In particular, the survival rates of AZT of the present invention stored at 60° C. for two weeks are about two times higher than that of Comparative Example 3.

Comparison of the survival rates of AZT stored at 60° C. for one week in Examples 9 to 12 with each other demonstrates that the addition of NaCl or mannitol increases heat stability of azithromycin more than the addition of propylene glycol or glycerine.

EXAMPLE 13 TO 17

To sterile purified water (50 mL), azithromycin (1.0 g) was added, agitated and dispersed. Separately, a polyvalent carboxylic acid was dissolved in a given amount in sterile purified water (80 mL) and sterile purified water was added to prepare 100 mL of a polyvalent carboxylic acid solution. To the azithromycin dispersed liquid, the polyvalent carboxylic acid solution (10 mL) was gradually added with agitation so that pH of the solution was maintained at 5.0 or higher. Concentration of the polyvalent carboxylic acid added in the composition is shown in Table 3.

After confirming that azithromycin was completely dissolved, ethanolamine (0.2 g) and NaCl (0.73 g) were added and dissolved with agitation. After confirming that the solution became clear, pH was adjusted to 7.0 with 1N-NaOH or 1N-HCl and sterile purified water was added to prepare 100 mL of the azithromycin-containing aqueous pharmaceutical compositions (Examples 13 to 17). Table 3 shows the formulations of the compositions and appearance of the compositions after the preparation.

TABLE 3

|  | Ex. 13 | Ex. 14 | Ex. 15 | Ex. 16 | Ex. 17 |
|---|---|---|---|---|---|
| AZT (w/v %) | 1.0 | 1.0 | 1.0 | 1.0 | 1.0 |
| monoethanolamine (w/v %) | 0.2 | 0.2 | 0.2 | 0.2 | 0.2 |
| tartaric acid (w/v %) | 0.22 | — | — | — | — |
| malic acid (w/v %) | — | 0.20 | — | — | — |
| maleic acid (w/v %) | — | — | 0.18 | — | — |
| fumaric acid (w/v %) | — | — | — | 0.18 | — |
| succinic acid (w/v %) | — | — | — | — | 0.18 |
| NaCl (w/v %) | 0.73 | 0.73 | 0.73 | 0.73 | 0.73 |
| 1N NaOH or 1N HCl | A.A. | A.A. | A.A. | A.A. | A.A. |
| water | A.A. | A.A. | A.A. | A.A. | A.A. |
| appearance after the preparation | clear | clear | clear | clear | clear |

Appearance of all the compositions was clear, which demonstrates that hardly water soluble azithromycin was completely dissolved.

EXAMPLES 18 TO 20

To sterile purified water (50 mL), azithromycin (1.0 g) was added, agitated and dispersed. Separately, citric acid monohydrate (1.9 g) was dissolved in sterile purified water (80 mL) and sterile purified water was added to prepare a citric acid solution (100 mL). To the azithromycin dispersed liquid, the citric acid solution (10 mL) was gradually added so that pH of the liquid was maintained at 5.0 or higher or 6.0 or higher. After confirming that azithromycin was completely dissolved, mannitol (1.61 g) and monoethanolamine (0.2 g) were added and dissolved with agitation. After confirming that the solution became clear, pH of the solution was adjusted to 7.0 with 1N-NaOH or 1N-HCl and sterile purified water was added to prepare 100 mL of the azithromycin-containing aqueous pharmaceutical compositions of the present invention (Examples 18 to 19).

To sterile purified water (60mL), citric acid monohydrate (0.19 g) was added and dissolved with agitation. To the solution, azithromycin (1.0 g) was added, agitated and dispersed. Agitation was continued until azithromycin was completely dissolved. After confirming that azithromycin was completely dissolved, mannitol (1.61 g) and monoethanolamine (0.2 g) were added and dissolved with agitation. After confirming that the solution became clear, pH of the solution was adjusted to 7.0 with 1N-NaOH or 1N-HCl and sterile purified water was added to prepare 100 mL of a comparative azithromycin-containing aqueous pharmaceutical composition (Example 20).

TEST EXAMPLE 3

The similar procedures to Test Example 1 were repeated to evaluate stability of the compositions of Examples 18 to 20.

Table 4 shows the lowest pH values of the azithromycin dispersed liquids during the preparation steps and results of stability tests thereof.

TABLE 4

|  | Ex. 18 | Ex. 19 | Ex. 20 |
|---|---|---|---|
| AZT (w/v %) | 1.0 | 1.0 | 1.0 |
| monoethanolamine (w/v %) | 0.2 | 0.2 | 0.2 |
| D-mannitol (w/v %) | 1.61 | 1.61 | 1.61 |
| citric acid•H$_2$O (w/v %) | 0.19 | 0.19 | 0.19 |
| 1N NaOH or 1N HCl | A.A. | A.A. | A.A. |
| water | A.A. | A.A. | A.A. |
| the lowest pH values during the preparation steps | 6.2 | 5.2 | 2.8 |

TABLE 4-continued

|  | Ex. 18 | Ex. 19 | Ex. 20 |
|---|---|---|---|
| survival rate of AZT after preparation (%) | 100.2 | 99.5 | 93.9 |
| survival rate of AZT stored at 60° C. for two weeks (%) | 61.2 | 60.8 | 57.4 |

The Lowest pH Values During the Azithromycin Dissolving Step:

During the preparation step in Example 20, the lowest pH value was found 2.8 which was observed just after azithromycin was added to the citric acid solution. In Examples 18 and 19, the lowest pH value was found 6.2 and 5.2, respectively.

Stability During Preparation Steps:

Survival rates of AZT after preparation show that azithromycin in the compositions of the present invention (Examples 18 and 19) was completely dissolved but not decomposed. In contrast, survival rate of AZT after preparation was decreased in the composition of Example 20, which shows that azithromycin was decomposed during the preparation steps.

The above data show that azithromycin was decomposed a little during the preparation steps wherein azithromycin was exposed to a lower pH condition such as pH2.8.

Heat Stability of Azithromycin:

It has been found that the composition of Example 20 had a little lower heat stability than those of Examples 18 and 19. This demonstrates that heat stability of azithromycin in the composition is lower if the composition is prepared by a method wherein azithromycin is liable to decompose, even if the formulation is the same.

EXAMPLES 21 TO 28 AND COMPARATIVE EXAMPLES 4 AND 5

To sterile purified water (50 mL), azithromycin dihydrate in a given amount was added, agitated and dispersed. Separately, citric acid monohydrate (10 g) was dissolved in sterile purified water (80 mL) and sterile purified water was added to prepare a citric acid solution (100 mL). To the azithromycin dispersed liquid, the citric acid solution was gradually added with agitation so that pH of the liquid was maintained at 5.0 or higher. After confirming that azithromycin was completely dissolved, the following additives were added in given amounts and dissolved with agitation.

Additives:
L-alanine
L-serine
monoethanolamine
glycine
ethylenediaminetetraacetic acid.2Na (0.5 w/v % aqueous solution previously prepared)
NaCl
benzalkonium chloride (0.5 w/v % aqueous solution previously prepared)

After confirming that the solution became clear, pH was adjusted to 7.0 with 1N-NaOH or 1N-HCl and sterile purified water was added to prepare 100 mL of the azithromycin-containing aqueous pharmaceutical composition of the present invention (Examples 21 to 28).

According to the similar method to Comparative Example 2, the composition of Comparative Example 4 was prepared.

To sterile purified water (50 mL), azithromycin dihydrate (1.05 g) was added, agitated and dispersed. Separately, citric acid monohydrate (10 g) was dissolved in sterile purified water (80 mL) and sterile purified water was added to prepare a citric acid solution (100 mL). To the azithromycin dispersed liquid, the citric acid solution (0.2 mL) was gradually added with agitation so that pH of the liquid was maintained at 5.0 or higher. Confirming that azithromycin was completely dissolved, monoethanolamine (0.2 g) was added and dissolved with agitation. Further, boric acid (1.5 g) and borax (0.3 g) were added and dissolved with agitation. After confirming that the solution became clear, pH was adjusted to 7.0 with 1N-NaOH or 1N-HCl and sterile purified water was added to prepare 100 mL of the azithromycin-containing aqueous pharmaceutical composition (Comparative Example 5).

TEST EXAMPLE 4

The azithromycin-containing aqueous pharmaceutical compositions prepared in the above Examples and Comparative Examples were evaluated for stability in terms of azithromycin concentration in the compositions.

The compositions (Examples 21 to 28 and Comparative Examples 4 and 5) were packed in glass vial and sealed with a lid, and then stored at 60° C. for one and two weeks. Then, azithromycin concentration in the composition just after prepared and after the storage at 60° C. was determined by HPLC. Stability was evaluated by comparing the azithromycin content just after the preparation with the azithromycin content in the composition after the storage at 60° C. Results are shown in Table 5.

TABLE 5

|  | Ex. 21 | Ex. 22 | Ex. 23 | Ex. 24 | Ex. 25 | Ex. 26 | Ex. 27 | Ex. 28 | Comp. Ex. 4 | Comp. Ex. 5 |
|---|---|---|---|---|---|---|---|---|---|---|
| AZT•2H$_2$O (w/v %) | 1.05 | 1.05 | 0.1 | 0.1 | 0.3 | 3.15 | 5.0 | 1.05 | 1.05 | 1.05 |
| L-alanine (w/v %) | 0.2 | — | — | — | — | — | — | — | — | — |
| L-serine (w/v %) | — | 0.2 | — | — | — | — | — | — | — | — |
| monoethanolamine (w/v %) | — | — | 0.5 | 0.01 | 0.02 | 0.04 | 0.04 | — | — | 0.02 |
| glycine (w/v %) | — | — | — | — | — | — | — | 4.0 | — | — |
| EDTA•2Na (w/v %) | — | — | — | — | 0.005 | 0.005 | — | — | — | — |
| citric acid•H$_2$O | 0.2 | 0.2 | 0.02 | 0.02 | 0.06 | 0.63 | 1.0 | 0.2 | 0.44 | 0.2 |

TABLE 5-continued

|  | Ex. 21 | Ex. 22 | Ex. 23 | Ex. 24 | Ex. 25 | Ex. 26 | Ex. 27 | Ex. 28 | Comp. Ex. 4 | Comp. Ex. 5 |
|---|---|---|---|---|---|---|---|---|---|---|
| $Na_2HPO_4 \cdot 12H_2O$ (w/v %) | — | — | — | — | — | — | — | — | 3.3 | — |
| NaCl (w/v %) | 0.7 | 0.7 | 0.8 | 0.8 | 0.8 | 0.6 | 0.45 | 0.7 | — | — |
| benzalkonium chloride (w/v %) | — | — | — | 0.005 | 0.002 | 0.002 | — | — | — | — |
| boric acid (w/v %) | — | — | — | — | — | — | — | — | — | 1.5 |
| borax (w/v %) | — | — | — | — | — | — | — | — | — | 0.3 |
| 1N NaOH or 1N HCl | A.A. | A.A. | A.A. | A.A. | A.A. | A.A. | A.A. | A.A. | — | A.A. |
| water | A.A. | A.A. | A.A. | A.A. | A.A. | A.A. | A.A. | A.A. | A.A. | A.A. |
| pH | 7.0 | 7.0 | 7.0 | 7.0 | 7.0 | 7.0 | 7.0 | 7.0 | 7.0 | 7.0 |
| survival rate of AZT stored at 60° C. for one week (%) | 73.8 | 74.9 | 73.4 | 76.2 | 76.4 | 74.3 | 76.1 | 72.6 | 50.0 | 15.2 |
| survival rate of AZT stored at 60° C. for two weeks (%) | 56.1 | 57.4 | 56.3 | 59.7 | 59.2 | 57.6 | 58.4 | 52.8 | 23.9 | 3.6 |

Heat Stability of Azithromycin:

It has been found that the compositions of the present invention had higher heat stability than that of Comparative Example 4. In particular, the survival rates of AZT in the compositions of the present invention stored at 60° C. for two weeks are two times higher than that of Comparative Example 4.

In addition, as shown in Comparative Example 5, the addition of boric acid or salts thereof to the composition decreased the azithromycin content but did not yield the effect of the present invention. This demonstrates that it is contraindicated to add boric acid or salts thereof to the composition of the present invention from the stability point of view.

EXAMPLES 29 TO 35 AND COMPARATIVE EXAMPLE 6

To sterile purified water (50 mL), azithromycin dihydrate (1.05 g) was added, agitated and dispersed. Separately, citric acid monohydrate (10 g) was dissolved in sterile purified water (80 mL) and sterile purified water was added to prepare a citric acid solution (100 mL). To the azithromycin dispersed liquid, the citric acid solution (2.1 mL) was gradually added with agitation so that pH was maintained at 4.0 or higher. After confirming that azithromycin was completely dissolved, the following additives in given amounts were added and dissolved with agitation.

Additives:
monoethanolamine (0.04 g)
NaCl (0.73 g)
ethylenediaminetetraacetic acid.2Na (1 mL of 0.5 w/v % solution previously prepared)

After confirming that the solution became clear, pH was adjusted to 5.0 to 8.0 with 1N-NaOH or 1N-HCl and sterile purified water was added to prepare 100 mL of the azithromycin-containing aqueous pharmaceutical composition of the present invention (Examples 29 to 35).

According to the similar manner to Comparative Example 2, the composition of Comparative Example 6 was prepared.

TEST EXAMPLE 5

The azithromycin-containing aqueous pharmaceutical compositions prepared in the above Examples and Comparative Example were evaluated for stability in terms of azithromycin concentration in the compositions.

The compositions thus prepared (Examples 29 to 35 and Comparative Example 6) were packed in glass vial, sealed with a lid, and stored at 60° C. for one and two weeks.

Then, azithromycin concentrations in the compositions were determined by HPLC. Stability was evaluated by comparing azithromycin concentration in the compositions just after the preparation with those after stored at 60° C. Results are shown in Table 6.

TABLE 6

|  | Ex. 29 | Ex. 30 | Ex. 31 | Ex. 32 | Ex. 33 | Ex. 34 | Ex. 35 | Comp. Ex. 6 |
|---|---|---|---|---|---|---|---|---|
| $AZT \cdot 2H_2O$ (w/v %) | 1.05 | 1.05 | 1.05 | 1.05 | 1.05 | 1.05 | 1.05 | 1.05 |
| monoethanolamine (w/v %) | 0.04 | 0.04 | 0.04 | 0.04 | 0.04 | 0.04 | 0.04 | — |
| $EDTA \cdot 2Na$ (w/v %) | 0.005 | 0.005 | 0.005 | 0.005 | 0.005 | 0.005 | 0.005 | — |
| citric acid·$H_2O$ (w/v %) | 0.21 | 0.21 | 0.21 | 0.21 | 0.21 | 0.21 | 0.21 | 0.44 |
| NaCl (w/v %) | 0.73 | 0.73 | 0.73 | 0.73 | 0.73 | 0.73 | 0.73 | — |
| $Na_2HPO_4 \cdot 12H_2O$ (w/v %) | — | — | — | — | — | — | — | 3.3 |
| 1N NaOH or 1N HCl | A.A. | A.A. | A.A. | A.A. | A.A. | A.A. | A.A. | — |
| water | A.A. | A.A. | A.A. | A.A. | A.A. | A.A. | A.A. | A.A. |
| pH | 5.0 | 5.5 | 6.0 | 6.5 | 7.0 | 7.5 | 8.0 | 7.0 |
| survival rate of AZT stored at 60° C. for one week (%) | 27.9 | 65.5 | 84.3 | 81.9 | 75.5 | 73.7 | 68.2 | 52.8 |

TABLE 6-continued

|  | Ex. 29 | Ex. 30 | Ex. 31 | Ex. 32 | Ex. 33 | Ex. 34 | Ex. 35 | Comp. Ex. 6 |
|---|---|---|---|---|---|---|---|---|
| survival rate of AZT stored at 60° C. for two weeks (%) | 6.6 | 35.7 | 57.8 | 57.7 | 57.3 | 52.0 | 48.7 | 26.1 |

Heat Stability of Azithromycin:

It has been found that the compositions of the present invention having pH of from 5.5 to 8.0 had higher heat stability than that of Comparative Example 6. In particular, it has been found that survival rates of AZT stored at 60° C. for two weeks (%) of the present invention having pH of from 6.0 to 7.5 were about two times that of Comparative Example 6, which shows excellent heat stability of the compositions of the present invention.

EXAMPLES 36 TO 40

To sterile purified water (50 mL), azithromycin dihydrate (1.05 g) was added, agitated and dispersed. Separately, citric acid monohydrate (10 g) was dissolved in sterile purified water (80 mL) and sterile purified water was added to prepare a citric acid solution (100 mL). To the azithromycin dispersed liquid, the citric acid solution (2.1 mL) was gradually added with agitation so that pH was maintained at 4.0 or higher. After confirming that azithromycin was completely dissolved, the following additives were added in given amounts.
Additives:
 monoethanolamine (0.04 g)
 D-mannitol (2.0 to 10 g)
 NaCl (0.3 to 2.0 g)
 ethylenediaminetetraacetic acid.2Na (1 mL of 0.5 w/v % aqueous solution previously prepared)

After confirming that the solution became clear, pH was adjusted to 7.0 with 1N-NaOH or 1N-HCl and sterile purified water was added to prepare 100 mL of the azithromycin-containing aqueous pharmaceutical composition of the present invention (Examples 36 to 40).

Test Example 6

The azithromycin-containing aqueous pharmaceutical compositions prepared in the above Examples were evaluated for stability in terms of the azithromycin concentration in the compositions.

The compositions thus prepared (Examples 36 to 40) were packed in glass vial, sealed with a lid and stored at 60° C. for one and two weeks. Then, azithromycin concentrations in the compositions just after the preparation and the storage were determined by HPLC. Stability was evaluated by comparing azithromycin concentration in the compositions just after the preparation with those after stored at 60° C. Results are shown in Table 7.

TABLE 7

|  | Ex. 36 | Ex. 37 | Ex. 38 | Ex. 39 | Ex. 40 |
|---|---|---|---|---|---|
| AZT•2H$_2$O (w/v %) | 1.05 | 1.05 | 1.05 | 1.05 | 1.05 |
| monoethanolamine (w/v %) | 0.04 | 0.04 | 0.04 | 0.04 | 0.04 |
| EDTA•2Na (w/v %) | 0.005 | 0.005 | 0.005 | 0.005 | 0.005 |
| citric acid•H$_2$O (w/v %) | 0.21 | 0.21 | 0.21 | 0.21 | 0.21 |
| NaCl (w/v %) | 0.3 | 2.0 | — | — | 0.4 |
| D-mannitol (w/v %) | — | — | 2.0 | 10 | 2.0 |
| 1N NaOH or 1N HCl | A.A. | A.A. | A.A. | A.A. | A.A. |
| water | A.A. | A.A. | A.A. | A.A. | A.A. |
| pH | 7.0 | 7.0 | 7.0 | 7.0 | 7.0 |
| survival rate of AZT stored at 60° C. for one week (%) | 77.8 | 76.3 | 78.3 | 77.2 | 75.5 |
| survival rate of AZT stored at 60° C. for two weeks (%) | 59.6 | 58.7 | 59.1 | 58.6 | 57.3 |

Heat Stability of Azithromycin:

It has been found survival rates of AZT stored at 60° C. for two weeks (%) of the present invention were about two times that of Comparative Example 6 in Table 6, which shows excellent heat stability of the compositions of the present invention.

EXAMPLES 41 TO 42

To sterile purified water (500 mL), azithromycin dihydrate (10.5 g) was added, agitated and dispersed. To the azithromycin dispersed liquid, citric acid monohydrate (2.1 g) was gradually added with agitation so that pH was maintained at 5.0 or higher. After confirming that azithromycin was completely dissolved, the following additives were added in given amounts and dissolved with agitation.
Additives:
 monoethanolamine (0.4 g)
 D-mannitol (45 g)
 NaCl (7.3 g)
 benzalkonium chloride (10 mL of 0.5 w/v % aqueous solution previously prepared)
 ethylenediaminetetraacetic acid.2Na (10 mL of 0.5 w/v % aqueous solution previously prepared)

After confirming that the solution became clear, pH was adjusted to 7.0 with 1N-NaOH or 1N-HCl and sterile purified water was added to prepare 1000 mL of the azithromycin-containing aqueous pharmaceutical composition of the present invention (Examples 41 and 42). The solution was filtered with membrane filter having pore diameter of 0.2 μm and packed in 5 mL plastic bottle for eye drops to prepare azithromycin-containing eye drops of the present invention.

TEST EXAMPLE 7

Stability of the above azithromycin-containing eye drops of the present invention was evaluated in terms of the azithromycin concentration in the eye drops.

The azithromycin-containing eye drops of the present invention were stored at 25° C. for three and six months. Then, azithromycin concentrations in the compositions just after the preparation and the storage at 25° C. were determined by HPLC. Stability was evaluated by comparing azithromycin concentration in the compositions just after the preparation with those after stored at 25° C. Results are shown in Table 8.

TABLE 8

|  | Ex. 41 | Ex. 42 |
|---|---|---|
| AZT•2H$_2$O (w/v %) | 1.05 | 1.05 |
| monoethanolamine (w/v %) | 0.04 | 0.04 |
| EDTA•2Na (w/v %) | 0.005 | 0.005 |
| citric acid•H$_2$O (w/v %) | 0.21 | 0.21 |
| NaCl (w/v %) | 0.73 | — |
| D-mannitol(w/v %) | — | 4.5 |
| benzalkonium chloride (w/v %) | 0.005 | 0.005 |
| 1N NaOH or 1N HCl | A.A. | A.A. |
| water | A.A. | A.A. |
| pH | 7.0 | 7.0 |
| survival rate of AZT stored at 25° C. for three months (%) | 94.8 | 95.6 |
| survival rate of AZT stored at 25° C. for six months (%) | 93.8 | 94.2 |

Heat Stability of Azithromycin:

Survival rates of azithromycin stored at 25° C. for three and six months were 90% or higher and it has been demonstrated that the eye drops of the present invention are excellent in stability for a long period of time.

EXAMPLE 43

Injection

The azithromycin-containing aqueous pharmaceutical composition of the present invention prepared in Example 1 was filtered with membrane filter, packed in 5mL glass ample and sealed to prepare an injection.

EXAMPLE 44

Nasal Drops

The azithromycin-containing aqueous pharmaceutical composition of the present invention prepared in Example 42 was filtered with membrane filter, packed in plastic container for nasal drops to prepare nasal drops.

EXAMPLE 45

Ear Drips

The azithromycin-containing aqueous pharmaceutical composition of the present invention prepared in Example 41 was filtered with membrane filter, packed in plastic container for ear drips to prepare ear drips.

EXAMPLE 46

Liniment

The azithromycin-containing aqueous pharmaceutical composition of the present invention prepared in Example 41 was filtered with membrane filter, packed in plastic container to prepare liniment.

EXAMPLE 47

Oral Formulation

The azithromycin-containing aqueous pharmaceutical composition of the present invention prepared in Example 42 was filtered with membrane filter, packed in glass container to prepare oral formulation.

What is claimed is:

1. An azithromycin-containing aqueous pharmaceutical composition, which comprises water, at least one member selected from the group consisting of azithromycin, and a pharmaceutically acceptable thereof in an amount of 0.1 to 5.0 w/v % as weight of azithromycin, and at least one additive for increasing heat stability of azithromycin in an aqueous solution selected from the group consisting of monoethanolamine, diethanolamine, triethanolamine, and a pharmaceutically acceptable salt thereof, and which does not comprise boric acid or pharmaceutically acceptable salts thereof, wherein:

the composition further comprises citric acid in an amount of 0.02 to 1.0 w/v %;

the composition has a pH of from 6.0 to 7.5;

the composition is a clear solution, and the composition has a heat stability such that a weight ratio of azithromycin content remaining in the composition after packing in a glass vial, sealed and stored at 60° C. for one week to the initial content of azithromycin in the composition is at least 70%.

2. The aqueous pharmaceutical composition of claim 1, wherein the composition further comprises at least one member selected from the group consisting of sodium chloride and mannitol.

3. The aqueous pharmaceutical composition of claim 1, wherein the composition has pH of from 6.0 to 6.5.

4. The aqueous pharmaceutical composition of claim 1, wherein the composition comprises:

at least one member selected from the group consisting of azithromycin and pharmaceutically acceptable salts thereof in an amount of 0.3 to 3.0 w/v % as weight of azithromycin.

5. The aqueous pharmaceutical composition of claim 1, wherein the composition comprises monoethanolamine.

6. The aqueous pharmaceutical composition of claim 2, wherein the composition comprises monoethanolamine.

7. The aqueous pharmaceutical composition of claim 3, wherein the composition comprises monoethanolamine.

8. A method for the preparation of an azithromycin-containing aqueous pharmaceutical composition of claim 1, which comprises:

(a) suspending at least one member selected from the group consisting of azithromycin, its anhydride, its hydrate, and pharmaceutically acceptable salts thereof in water to form an azithromycin-containing liquid, (b) adding to the azithromycin-containing liquid a polyvalent carboxylic acid to provide a second liquid, (c) adding to the second liquid at least one member selected from the group consisting of monoethanolamine, diethanolamine, triethanolamine, epsilon-amino caproic acid, glycine, glutamic acid, aspartic acid, alanine, serine, and pharmaceutically acceptable salts thereof to produce a third liquid wherein the azithromycin-containing liquid, second liquid and third liquid are maintained at pH of 5.0 or higher throughout the method.

* * * * *